United States Patent
Wang et al.

(10) Patent No.: US 12,037,316 B2
(45) Date of Patent: Jul. 16, 2024

(54) ENERGY-SAVING METHOD FOR PREPARING ELECTRONIC-GRADE CARBONATE

(71) Applicant: TIANJIN UNIVERSITY OF SCIENCE & TECHNOLOGY, Tianjin (CN)

(72) Inventors: Hongxing Wang, Tianjin (CN); Haiyong Li, Tianjin (CN); Guangqiang Zheng, Tianjin (CN); Fei Li, Tianjin (CN)

(73) Assignee: TIANJIN UNIVERSITY OF SCIENCE & TECHNOLOGY, Tianjin (CN)

( * ) Notice: Subject to any disclaimer, the term of this patent is extended or adjusted under 35 U.S.C. 154(b) by 0 days.

(21) Appl. No.: 18/254,846

(22) PCT Filed: Oct. 11, 2022

(86) PCT No.: PCT/CN2022/124504
§ 371 (c)(1),
(2) Date: May 26, 2023

(87) PCT Pub. No.: WO2023/178991
PCT Pub. Date: Sep. 28, 2023

(65) Prior Publication Data
US 2024/0034714 A1 Feb. 1, 2024

(51) Int. Cl.
*C07C 68/08* (2006.01)
*C07C 68/06* (2020.01)

(52) U.S. Cl.
CPC .............. *C07C 68/08* (2013.01); *C07C 68/06* (2013.01); *Y02P 20/10* (2015.11)

(58) Field of Classification Search
CPC .......... C07C 68/08; C07C 68/06; Y02P 20/10
See application file for complete search history.

(56) References Cited

FOREIGN PATENT DOCUMENTS

| CN | 105968004 A | 9/2016 |
|---|---|---|
| CN | 109503375 A | 3/2019 |

(Continued)

OTHER PUBLICATIONS

PCT/CN2022/124504—Written Opinion of the International Searching Authority, mailed Oct. 15, 2021, 5 pages. (English translation).

*Primary Examiner* — Thuan D Dang
(74) *Attorney, Agent, or Firm* — Getech Law LLC; Jun Ye

(57) ABSTRACT

The present disclosure discloses an energy-saving method for preparing electronic-grade carbonate, including the following steps that: industrial-grade dimethyl carbonate and anhydrous ethanol enter a reaction process after being preheated by a preheater, and are subjected to an esterification reaction under the action of a catalyst to obtain a mixture containing dimethyl carbonate, ethyl methyl carbonate and diethyl carbonate, and an azeotrope of dimethyl carbonate and methanol; the above-mentioned mixture enters a recovery process of dimethyl carbonate to recover unreacted dimethyl carbonate; a mixture of ethyl methyl carbonate and diethyl carbonate then enters a crude separation process to obtain crude ethyl methyl carbonate and crude diethyl carbonate; and the crude ethyl methyl carbonate is subjected to a refining process of ethyl methyl carbonate to obtain electronic-grade ethyl methyl carbonate, and the crude diethyl carbonate is subjected to a refining process of diethyl carbonate to obtain electronic-grade diethyl carbonate.

8 Claims, 3 Drawing Sheets

(56) References Cited

FOREIGN PATENT DOCUMENTS

| | | |
|---|---|---|
| CN | 110845334 A | 2/2020 |
| CN | 112142599 A | 12/2020 |
| CN | 113582845 A | 11/2021 |
| CN | 114380692 A | 4/2022 |
| JP | H0710811 A | 1/1995 |

ENERGY-SAVING METHOD FOR PREPARING ELECTRONIC-GRADE CARBONATE

FIELD

The present disclosure relates to the technical field of chemical engineering, in particular to an energy-saving method for preparing electronic-grade carbonate, and specifically, an energy-saving method for the preparation of electronic-grade ethyl methyl carbonate and diethyl carbonate.

BACKGROUND

Carbonates are widely used in various fields of chemical industry, especially diethyl carbonate (DEC) and ethyl methyl carbonate (EMC), etc. are commonly used as chemical raw materials or synthesis intermediates, however, the purity of diethyl carbonate (DEC) and ethyl methyl carbonate (EMC) obtained by a preparation method in the prior art is low and the preparation energy consumption is high, and an energy-saving method for the preparation of electronic-grade ethyl methyl carbonate and diethyl carbonate urgently needs further research and development.

CN111704547A discloses "Device and method for producing dimethyl carbonate through coupling of heat pump rectification and melt crystallization", a final product of this application is DMC, by using a reactive distillation column and a crystallization method, raw materials methanol, propylene carbonate and a catalyst are sent into the reactive distillation column, a mixture containing DMC and methanol is extracted from the top of the column, DMC is separated by using the crystallization method, and then methanol is recovered through the column. In terms of energy saving, gas phases at the top of the reactive distillation column and at the top of a methanol recovery column are directly compressed by using a heat pump technology, respectively, and then are heated by a reboiler of the reactive distillation column and a reboiler of a methanol column, respectively.

CN107400055A discloses "Method and device for rectifying purification of battery-grade dimethyl carbonate", a final product of this application is battery-grade DMC, and two dividing wall columns are subjected to differential pressure coupling.

CN105669451A discloses "Dividing wall thermally coupled distillation method and device for battery-grade dimethyl carbonate", this application produces battery-grade DMC, wherein one dividing wall column is used, and a certain proportion of an additive is added, and a front fraction is removed by controlling the temperature at the top of the column and an extraction flow rate in an early stage, which is similar to batch column operation.

CN103408428A discloses "Process for producing dimethyl carbonate from industrial synthetic gas", this application produces DMC, wherein methyl nitrite is first produced through oxidative esterification with industrial-grade nitric oxide, oxygen and methanol as raw materials, and then industrial-grade carbon monoxide and methyl nitrite are subjected to carbonylation to produce dimethyl carbonate. A pre-esterification column and an esterification column (denitrification) involve a reactive distillation column and a heat pump. The pre-esterification column involves an indirect heat pump, i.e. heat exchange using a circulating heat agent, a pressurizing column involves a direct heat pump as well as various heat exchange energy saving, a gas phase at the top of the column is compressed by a compressor to provide a heat source for a column bottom, a methanol column involves a direct heat pump, a gas phase at the top of the column is compressed by a compressor to provide a heat source for a column bottom, a product column involves a direct heat pump, a gas phase at the top of the column is compressed by a compressor to provide a heat source for a column bottom, and a wastewater column involves a direct heat pump, a gas phase at the top of the column is compressed by a compressor to provide a heat source for a column bottom.

CN101367733A discloses "Heat pump distillation device and process for diethyl carbonate", this application produces DEC, and a main process includes sending raw materials ethanol and DMC and a catalyst (sodium methoxide) into a reactive distillation column, extracting ethanol, methanol and DMC from the top of the column, extracting a mixed liquid (DEC, a small amount of DMC and heavy components) from the bottom of the column, allowing a material discharged from the the top of the column to enter a light component removal column, extracting methanol and DMC from the top of the column, extracting ethanol from the bottom of the column, allowing the mixed liquid extracted from the bottom of the reactive distillation column to enter a heavy component removal column, extracting DEC from the top of the column, extracting the heavy components from the bottom of the column, and allowing DEC extracted from the top of the column to enter a DEC refining column to obtain the product DEC.

CN101367734A discloses "Heat pump distillation device and process for diethyl carbonate", this application produces DEC, and a main process includes sending raw materials ethanol and DMC and a catalyst (sodium methoxide) into a reactive distillation column, extracting ethanol, methanol and DMC from the top of the column, extracting a mixed liquid (DEC, a small amount of DMC and heavy components) from the bottom of the column, allowing a material discharged from the the top of the column to enter a light component removal column, extracting methanol and DMC from the top of the column, extracting ethanol from the bottom of the column, allowing the mixed liquid extracted from the bottom of the reactive distillation column to enter a heavy component removal column, extracting DEC from the top of the column, extracting the heavy components from the bottom of the column, and allowing DEC extracted from the top of the column to enter a DEC refining column to obtain the product DEC.

CN104718183A discloses "Method for manufacturing diethyl carbonate", and this application produces DEC, and relates to a method for manufacturing diethyl carbonate by reactive distillation comprising continuously feeding dimethyl carbonate and ethanol into a reactive distillation column to simultaneously carry out transesterification and distillation in the reactive distillation column in the presence of a transesterification catalyst.

CN201665644U discloses "Device for producing ethyl methyl carbonate by transesterification", this application produces EMC, i.e., through a reaction column, a column bottom is connected to two rectifying stills, in which dimethyl carbonate and ethanol are extracted and returned to the reaction column, and the rectifying stills are operated under vacuum and equipped with DCS automatic control.

CN106699565A discloses "Device and method for energy saving and consumption reduction of dimethyl carbonate device", this application produces DMC, wherein raw materials ethanol, propylene carbonate and a methanol alkaline catalyst are first sent into a reactive distillation column, an azeotrope of DMC and methanol is extracted from the top of the column, a mixture is extracted from the bottom of the column, the azeotrope extracted from the top of the column is sent into a pressurizing column, and a gas phase extracted from the top of the column is allowed to enter a methanol column, wherein the gas phase at the top of the pressurizing column provides a heat source for a reboiler of the reactive distillation column, and a methanol refining column adopts a direct heat pump method.

CN112142599B discloses "Low-energy-consumption and green carbonate product production process and system", this application produces DMC, a reaction section of a DMC unit includes a pre-reactor and a reactive distillation column, the pre-reactor is a fixed bed reactor, and the reactive distillation column adopts heat pump distillation; a distillation section of the DMC unit includes a pressurizing column, a methanol column, a DMC refining column and a methanol recovery column, wherein a pressurizing distillation column and a methanol distillation column adopt heat pump distillation. A reaction section of an EMC unit includes a pre-reactor and a reactive distillation column, the pre-reactor is a fixed bed reactor; a distillation section of the EMC units includes a DMC recovery column and an EMC separation column, a material extracted from the side of the EMC separation column enters an EMC collection unit, and a material extracted from the bottom of the EMC separation column enters a DEC collection unit.

CN110845334A discloses "Device and method for preparing battery-grade ethyl methyl carbonate from dimethyl carbonate and ethanol", wherein ethanol and DMC are preheated and sent into a pre-reactor, followed by entering a reactive distillation column, mixed esters extracted from the bottom of the column are sent into a diethyl carbonate removal column, a material extracted from the top of the column is sent into an EMC refining column, a gas phase at the top of the diethyl carbonate removal column is compressed to provide a heat source for a reboiler of the reactive distillation column, and the EMC refining column adopts a heat pump technology.

CN106699564A discloses "Method and device for producing ethyl methyl carbonate by adopting an azeotropic reaction distillation dividing wall column", wherein a dividing wall distillation column is used to integrate a common distillation section, a reaction section, a primary distillation zone, a common stripping section, etc. into one column, i.e., a dividing wall column, and a crude product is sent to a purification column which uses a heat pump technology.

SUMMARY

An object of the present disclosure is to provide an energy-saving method for preparing electronic-grade carbonate in response to the technical defects existing in the prior art.

Another object of the present disclosure is to provide an energy-saving system for preparing electronic-grade carbonate.

The technical solutions used to achieve the objects of the present disclosure are as follows:
provided is an energy-saving method for preparing electronic-grade carbonate, wherein industrial-grade dimethyl carbonate and anhydrous ethanol are subjected to an esterification reaction under the action of a catalyst after being preheated to obtain a mixture containing dimethyl carbonate, ethyl methyl carbonate and diethyl carbonate, and an azeotrope of dimethyl carbonate and methanol;

unreacted dimethyl carbonate is recovered from the mixture containing dimethyl carbonate, ethyl methyl carbonate and diethyl carbonate; and a mixture of ethyl methyl carbonate and diethyl carbonate is subjected to crude separation to obtain crude ethyl methyl carbonate and crude diethyl carbonate;

the crude ethyl methyl carbonate is refined to obtain electronic-grade ethyl methyl carbonate, and the crude diethyl carbonate is refined to obtain electronic-grade diethyl carbonate; and the azeotrope of dimethyl carbonate and methanol is subjected to refining of methanol to obtain dimethyl carbonate and methanol.

In the above technical solution, the preparation method includes a reaction process, a recovery process of dimethyl carbonate, a crude separation process, a refining process of ethyl methyl carbonate, a refining process of diethyl carbonate, and a refining process of dimethyl carbonate and methanol;

industrial-grade dimethyl carbonate and anhydrous ethanol enter the reaction process after being preheated by a preheater, and are subjected to an esterification reaction under the action of a catalyst to obtain a mixture containing dimethyl carbonate, ethyl methyl carbonate and diethyl carbonate, and an azeotrope of dimethyl carbonate and methanol;

the mixture containing dimethyl carbonate, ethyl methyl carbonate and diethyl carbonate enters the recovery process of dimethyl carbonate to recover unreacted dimethyl carbonate;

a mixture of ethyl methyl carbonate and diethyl carbonate then enters the crude separation process to obtain crude ethyl methyl carbonate and crude diethyl carbonate;

the crude ethyl methyl carbonate is subjected to the refining process of ethyl methyl carbonate to obtain electronic-grade ethyl methyl carbonate, and the crude diethyl carbonate is subjected to the refining process of diethyl carbonate to obtain electronic-grade diethyl carbonate; and the azeotrope of dimethyl carbonate and methanol is subjected to the refining process of dimethyl carbonate and methanol to obtain dimethyl carbonate and methanol;

wherein the reaction process is thermally integrated and coupled with the refining process of dimethyl carbonate and methanol for energy saving, the recovery process of dimethyl carbonate is thermally integrated and coupled with the crude separation process for energy saving, the refining process of ethyl methyl carbonate uses thermal integration and coupling for energy saving, the refining process of dimethyl carbonate and methanol uses mechanical vapor recompression for energy saving, and the refining process of ethyl methyl carbonate uses mechanical vapor recompression for energy saving.

In the above technical solution, the reaction process includes a pre-reactor and an EMC reactive distillation column;

the recovery process of dimethyl carbonate includes a DMC recovery column and an anti-disproportionation reactor;

the crude separation process includes a crude separation column;

the refining process of ethyl methyl carbonate includes an EMC light component removal column and an EMC heavy component removal column;

the refining process of diethyl carbonate includes a DEC light component removal column and a DEC heavy component removal column; and the refining process of dimethyl carbonate and methanol includes a pressurizing column, an atmospheric column, a methanol refining column and a DMC refining column.

In the above technical solution, in the reaction process, industrial-grade dimethyl carbonate and ethanol enter the EMC reactive distillation column after being preheated by the pre-reactor, the EMC reactive distillation column is provided with a solid catalyst to catalyze the reaction, and a material discharged from the bottom of the EMC reactive distillation column enters the DMC recovery column;

in the recovery process of dimethyl carbonate, a part of a material extracted from the top of the DMC recovery column is sent back to the EMC reactive distillation column, and the other part of the material extracted from the top of the DMC recovery column enters the anti-disproportionation reactor; DMC/EMC/DEC produced by the anti-disproportionation reactor is conveyed to the DMC recovery column; and a material discharged from the bottom of the DMC recovery column enters the crude separation column;

in the crude separation process, a material discharged from the top of the crude separation column enters the EMC light component removal column, and a material extracted from the bottom of the crude separation column enters the DEC light component removal column;

in the refining process of ethyl methyl carbonate, a material discharged from the top of the EMC light component removal column enters the DMC recovery column, a material discharged from the bottom of the EMC light component removal column enters the EMC heavy component removal column, a material extracted from the side of the EMC heavy component removal column is electronic-grade EMC, a material discharged from the bottom of the EMC heavy component removal column enters the crude separation column, and a material discharged from the top of the EMC heavy component removal column enters the EMC light component removal column;

in the refining process of diethyl carbonate, a material extracted from the bottom of the DEC light component removal column enters the DEC heavy component removal column, a material extracted from the top of the DEC heavy component removal column is sent back to the DEC light component removal column, a material extracted from the bottom of the DEC heavy component removal column is a DEC high-boiling residue, a part of a material extracted from the side of the DEC heavy component removal column is an electronic-grade DEC product, and a part of the material extracted from the side of the DEC heavy component removal column is conveyed to the anti-disproportionation reactor; and in the refining process of dimethyl carbonate and methanol, a material discharged from the top of the EMC reactive distillation column, namely the azeotrope of DMC and methanol enters a pressurizing column, a material discharged from the top of the pressurizing column enters the atmospheric column, a material discharged from the bottom of the pressurizing column enters the DMC refining column, a material discharged from the DMC refining column is a DMC high-boiling residue, a material discharged from the top of the atmospheric column enters the pressurizing column, a material discharged from the bottom of the atmospheric column enters the methanol refining column, and a material extracted from the side of the methanol refining column is a methanol by-product.

In the above technical solution, a gas phase at the top of the crude separation column provides a partial heat source for a reboiler of the DMC recovery column; and a gas phase at the top of the pressurizing column provides a partial heat source for a reboiler of the EMC reactive distillation column.

In the above technical solution, a gas phase at the top of the atmospheric column is converted to secondary steam under the action of a compressor of the atmospheric column to provide a heat source for a reboiler of the atmospheric column.

In the above technical solution, a gas phase at the top of the methanol refining column is converted to secondary steam under the action of a compressor of a methanol column to provide a heat source for a reboiler of the methanol refining column.

In the above technical solution, the mechanical vapor recompression for energy saving in the refining process of ethyl methyl carbonate includes an EMC compressor, secondary steam compressed by an EMC compressor is delivered to a reboiler of the EMC light component removal column and a reboiler of the EMC heavy component removal column, respectively, and is heated, and then the heated material passes through the following two branches, respectively;

a branch 1 where the steam is cooled into water after passing through the reboiler of the EMC light component removal column, and enters a condenser of the EMC light component removal column for heat exchange and partial vaporization, and the generated steam continues to enter the EMC compressor;

a branch 2 where the steam is cooled into water after passing through the reboiler of the EMC heavy component removal column, and enters a condenser of the EMC heavy component removal column for heat exchange and partial vaporization, and the generated steam continues to enter the compressor; and recycling is performed through the branch 1 and the branch 2.

In the above technical solution, operating parameters of the pre-reactor are as follows:

| Name | Parameter range | Optimal operating parameter |
| --- | --- | --- |
| Operating temperature (° C.) | 110-130 | 115 |
| Operating pressure kPaA | 300-900 | 400~500 |

Operating parameters of the anti-disproportionation reactor are as follows:

| Name | Parameter range | Optimal operating parameter |
| --- | --- | --- |
| Operating temperature (° C.) | 110-130 | 115 |
| Operating pressure kPaA | 300-900 | 400~500 |

Operating parameters of the EMC reactive distillation column are as follows:

| Name | Parameter range | Optimal operating parameter |
|---|---|---|
| Column top temperature (° C.) | 64 | / |
| Column bottom temperature (° C.) | 105 | / |
| Operating pressure kPaA | atmospheric pressure | / |
| Reflux ratio | 2~6 | 4 |
| The number of theoretical plates | 30~60 | 50 |
| Feed position | 30~50 | 40 |
| Side extraction | / | / |

Operating parameters of the DMC recovery column are as follows:

| Name | Parameter range | Optimal operating parameter |
|---|---|---|
| Column top temperature (° C.) | 50~55 | 52 |
| Column bottom temperature (° C.) | 75~80 | 77 |
| Operating pressure kPaA | 25~40 | 30 |
| Reflux ratio | 5~10 | 7 |
| The number of theoretical plates | 30~60 | 50 |
| Feed position | 10~30 | 20 |
| Side extraction | / | / |

Operating parameters of the crude separation column are as follows:

| Name | Parameter range | Optimal operating parameter |
|---|---|---|
| Column top temperature (° C.) | 101~150 | 106 |
| Column bottom temperature (° C.) | 128~135 | 130 |
| Operating pressure kPaA | 90~200 | 30 |
| Reflux ratio | 1~10 | 3 |
| The number of theoretical plates | 30~60 | 50 |
| Feed position | 10~30 | 20 |
| Side extraction | / | / |

Operating parameters of the EMC light component removal column are as follows:

| Name | Parameter range | Optimal operating parameter |
|---|---|---|
| Column top temperature (° C.) | 50~60 | 55 |
| Column bottom temperature (° C.) | 70~80 | 75 |
| Operating pressure kPaA | 20~30 | 25 |
| Reflux feed ratio | 1~5 | 3 |
| The number of theoretical plates | 50~60 | 50 |
| Feed position | 10~30 | 20 |
| Side extraction | / | 1 |

Operating parameters of the EMC heavy removal column are as follows:

| Name | Parameter range | Optimal operating parameter |
|---|---|---|
| Column top temperature (° C.) | 50~60 | 55 |
| Column bottom temperature (° C.) | 70~80 | 75 |
| Operating pressure kPaA | 20~30 | 25 |
| Reflux feed ratio | 1~5 | 3 |
| The number of theoretical plates | 50~60 | 50 |
| Feed position | 40~50 | 45 |
| Side extraction | 20 | / |

Operating parameters of the DEC light component removal column are as follows:

| Name | Parameter range | Optimal operating parameter |
|---|---|---|
| Column top temperature (° C.) | 50~60 | 55 |
| Column bottom temperature (° C.) | 128~150 | 130 |
| Operating pressure kPaA | 101~200 | 105 |
| Reflux feed ratio | 1~5 | 3 |
| The number of theoretical plates | 50~60 | 50 |
| Feed position | 10~30 | 20 |
| Side extraction | / | / |

Operating parameters of the DEC heavy component removal column are as follows:

| Name | Parameter range | Optimal operating parameter |
|---|---|---|
| Column top temperature (° C.) | 85~90 | 88 |
| Column bottom temperature (° C.) | 90~100 | 95 |
| Operating pressure kPaA | 20~40 | 30 |
| Reflux feed ratio | 1~5 | 3 |
| The number of theoretical plates | 50~60 | 50 |
| Feed position | 40~50 | 45 |
| Side extraction | 20 | / |

Operating parameters of the pressurizing column are as follows:

| Name | Parameter range | Optimal operating parameter |
|---|---|---|
| Column top temperature (° C.) | 130~150 | 140 |
| Column bottom temperature (° C.) | 170~190 | 95 |
| Operating pressure kPaA | 700~1000 | 900 |
| Reflux feed ratio | 1~5 | 3 |
| The number of theoretical plates | 50~60 | 50 |
| Feed position | 30~50 | 40 |
| Side extraction | / | / |

Operating parameters of the atmospheric column are as follows:

| Name | Parameter range | Optimal operating parameter |
| --- | --- | --- |
| Column top temperature (° C.) | 64 | / |
| Column bottom temperature (° C.) | 66 | / |
| Operating pressure kPaA | 101~110 | 105 |
| Reflux feed ratio | 1~5 | 3 |
| The number of theoretical plates | 50~60 | 50 |
| Feed position | 30~50 | 40 |
| Side extraction | / | / |

Operating parameters of the DMC refining column are as follows:

| Name | Parameter range | Optimal operating parameter |
| --- | --- | --- |
| Column top temperature (° C.) | 91 | / |
| Column bottom temperature (° C.) | 94 | / |
| Operating pressure kPaA | 101~110 | 105 |
| Reflux feed ratio | 1~5 | 3 |
| The number of theoretical plates | 50~60 | 50 |
| Feed position | 30~50 | 40 |
| Side extraction | 20 | / |

Operating parameters of the methanol refining column are as follows:

| Name | Parameter range | Optimal operating parameter |
| --- | --- | --- |
| Column top temperature (° C.) | 64 | / |
| Column bottom temperature (° C.) | 66 | / |
| Operating pressure kPaA | 101~110 | 105 |
| Reflux feed ratio | 1~5 | 3 |
| The number of theoretical plates | 50~60 | 50 |
| Feed position | 30~50 | 40 |
| Side extraction | 20 | / |

Compared with the prior art, the method of the present disclosure has the following beneficial effects:

1. in the present disclosure, through the EMC reactive distillation column, methanol and DMC are separated at the top of the column, industrial-grade methanol and DMC are prepared through the pressurizing column, the atmospheric column, the DMC refining column and a methanol recovery column, and after the material discharged from the bottom of the EMC reactive distillation column passes through the DMC recovery column, and the crude separation column, electronic-grade EMC is prepared by the EMC light component removal column and the EMC heavy component removal column, and electronic-grade DEC is prepared by the DEC light component removal column and the DEC heavy component removal column, with high product quality and high yield. In addition, the method of the present disclosure has a higher degree of continuity and more stable and reliable quality.

2. In the present disclosure, the DMC recovery column and the crude separation column are thermally coupled under differential pressure, and the DEC light component removal column and the DEC heavy component removal column are thermally coupled under differential pressure. The DMC recovery column is operated under reduced pressure, the temperature at the bottom of the column is about 76° C., and the crude separation column is operated under atmospheric pressure, and the temperature of the gas phase at the top of the column is 106° C., load liquid of the two columns is close to each other, so the temperature difference and the load meet the requirements of thermal coupling. The same applies to the thermal coupling of the DEC light component removal column and the DEC heavy component removal column. The two thermally coupled columns should firstly meet a certain temperature difference between a gas phase at the top of a high-pressure column and the bottom of a low-pressure column, and its heat transfer rate should be within a reasonable range; and the two thermally coupled columns also needs to meet a condensing load of the gas phase at the top of the high-pressure column to be at least close to a heating load of the low-pressure column. In addition, the atmospheric column and the methanol refining column use a direct heat pump technology (the gas phase at the top of the column is directly compressed to heat the reboiler at the bottom of the column), and the EMC light component removal column and the EMC heavy component removal column use an indirect heat pump technology (water is used as an intermediate circulating medium, the top of the column is heated, and the gas phase is compressed to provide a heat source for the reboiler at the bottom of the column), and the above energy-saving solutions work in synergy, with low energy consumption.

3. The method of the present disclosure uses the pre-reactor and the reactive distillation column to prepare EMC and DEC, the pre-reactor is connected to the EMC reactive distillation column, the bottom of the EMC reactive distillation column is connected to the DMC recovery column to recover unreacted DMC, the pre-reactor is disposed so that ethanol is almost completely reacted.

4. The method of the present disclosure can adjust a yield ratio of EMC to DEC by using the anti-disproportionation reactor, the yield ratio can be adjusted to a greater extent, or no DEC can be produced to better meet the market demand, specifically, by adjusting the flow rate of DEC entering the anti-disproportionation reactor, DMC and DEC enter the anti-disproportionation reactor in a flow rate proportion to produce EMC, and the conversion rate of DEC is 20% to 70%.

1—Pre-reactor, 2—EMC reactive distillation column, 3—DMC recovery column, 4—anti-disproportionation reactor, 5—crude separation column, 6—EMC light component removal column, 7—EMC heavy component removal column, 8—DEC light component removal column, 9—DEC heavy component removal column, 10—pressurizing column, 11—atmospheric column, 12—methanol refining column, 13—DMC refining column, 14—industrial-grade dimethyl carbonate feeding pipeline, 15—ethanol feeding pipeline, 16—first connection pipeline, 17—second connection pipeline, 18—column top gas phase pipeline, 19—reboiler of DMC recovery column, 20—DEC high-boiling residue discharge pipeline, 21—EMC side extraction outlet, 22—electronic-grade DEC product output pipeline, 23—reboiler of EMC reactive distillation column, 24—DMC high-boiling residue discharge pipeline, 25—compressor of atmospheric column, 26—EMC compressor, 27—methanol by-product discharge pipeline, 28—reboiler of DEC heavy component removal column, 29—reboiler of methanol refining column, 30—compressor of methanol column, 31—gas-liquid separation tank, 32—first branch pipe, 33—second branch pipe, 34—reboiler of EMC light component removal column, 35—reboiler of EMC heavy component removal column, 36—reboiler of atmospheric column, 37—condenser of EMC heavy component removal column, 38—condenser of EMC light component removal column.

DETAILED DESCRIPTION OF THE EMBODIMENTS

The present disclosure is described in further detail below in connection with specific examples. It should be understood that the specific examples described herein are intended to explain the present disclosure only and are not intended to limit the present disclosure.

Example 1

Figure 1:
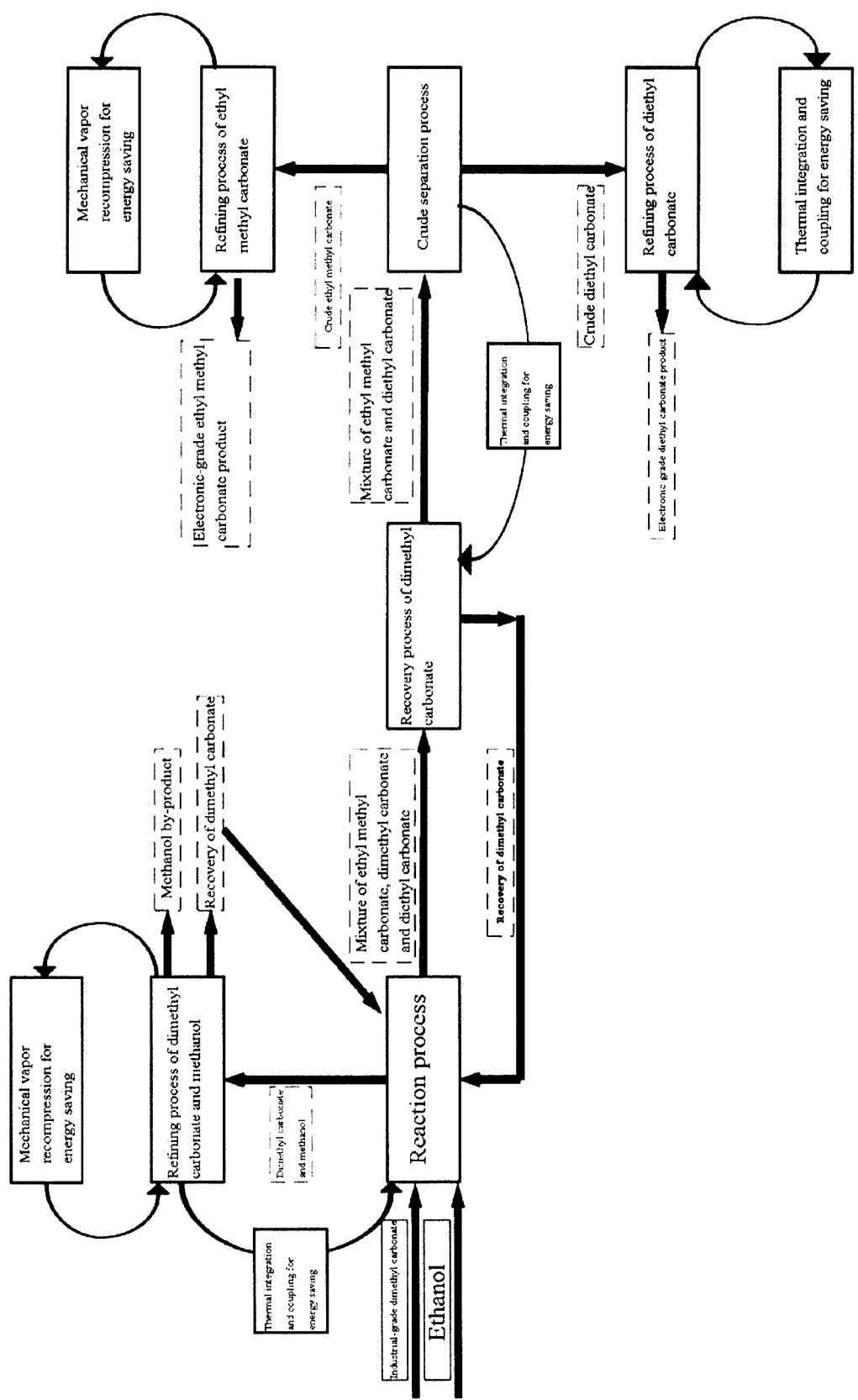
FIG. 1 is a schematic diagram of a preparation process in Example 1 of the present disclosure.

As shown in FIG. 1, an energy-saving method for preparing electronic-grade carbonate includes a reaction process, a recovery process of dimethyl carbonate, a crude separation process, a refining process of ethyl methyl carbonate, a refining process of diethyl carbonate, and a refining process of dimethyl carbonate and methanol;
  industrial-grade dimethyl carbonate and anhydrous ethanol enter the reaction process after being preheated by a preheater, and are subjected to esterification reaction under the action of a catalyst to obtain a mixture containing dimethyl carbonate, ethyl methyl carbonate and diethyl carbonate, and an azeotrope of dimethyl carbonate and methanol;
  the mixture containing dimethyl carbonate, ethyl methyl carbonate and diethyl carbonate enters the recovery process of dimethyl carbonate to recover unreacted dimethyl carbonate;
  a mixture of ethyl methyl carbonate and diethyl carbonate then enters the crude separation process to obtain crude ethyl methyl carbonate and crude diethyl carbonate;
  the crude ethyl methyl carbonate is subjected to the refining process of ethyl methyl carbonate to obtain electronic-grade ethyl methyl carbonate, and the crude diethyl carbonate is subjected to the refining process of diethyl carbonate to obtain electronic-grade diethyl carbonate; and
  the azeotrope of dimethyl carbonate and methanol is subjected to the refining process of dimethyl carbonate and methanol to obtain dimethyl carbonate and methanol.
  Wherein the reaction process is thermally integrated and coupled with the refining process of dimethyl carbonate and methanol for energy saving, the recovery process of dimethyl carbonate is thermally integrated and coupled with the crude separation process for energy saving, the refining process of ethyl methyl carbonate uses thermal integration and coupling for energy saving, the refining process of dimethyl carbonate and methanol uses mechanical vapor recompression for energy saving, and the refining process of ethyl methyl carbonate uses mechanical vapor recompression for energy saving.

Example 2

Figure 2:
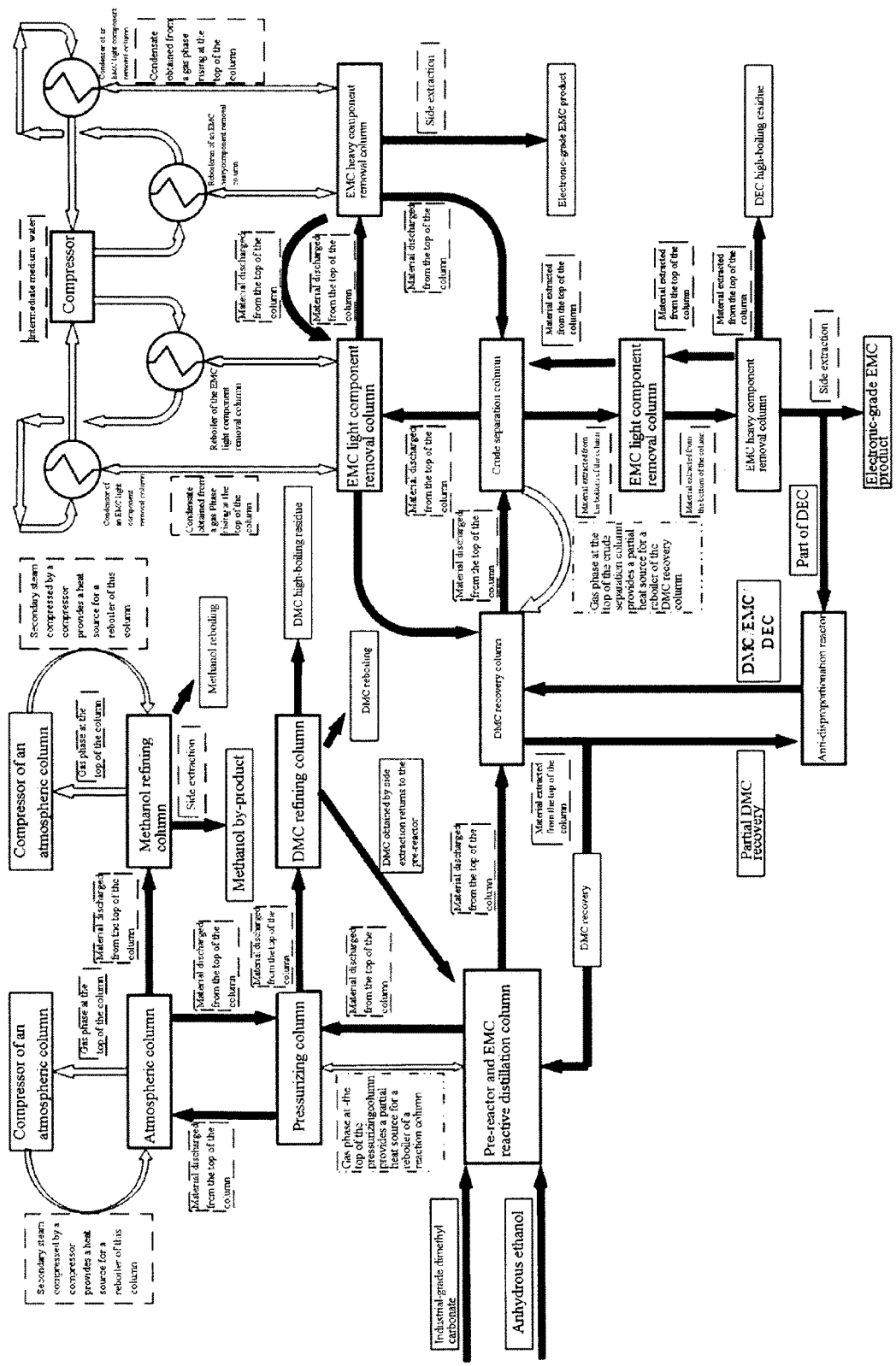
FIG. 2 is a diagram of a system in Example 2 of the present disclosure.

As shown in FIG. 2, this example provides further detailed descriptions of equipment for each process based on Example 1.
  The reaction process includes a pre-reactor 1 and an EMC reactive distillation column 2;
    the recovery process of dimethyl carbonate includes a DMC recovery column 3;
    the crude separation process includes a crude separation column 5;
    the refining process of ethyl methyl carbonate includes an EMC light component removal column 6 and an EMC heavy component removal column 7;
    the refining process of diethyl carbonate includes a DEC light component removal column 8 and a DEC heavy component removal column 9;
    the refining process of dimethyl carbonate and methanol includes a pressurizing column 10, an atmospheric column 11, a methanol refining column 12 and a DMC refining column 13;
  industrial-grade dimethyl carbonate and anhydrous ethanol enter the pre-reactor 1 after being preheated by a preheater for a reaction, and the resulting reaction solution then enters the EMC reactive distillation column 2, and the EMC reactive distillation column 2 is provided with a catalytic filler containing a solid catalyst in a lower middle part, with no subsequent catalyst separation process, and preferably, a main component of the solid catalyst is silica, and the solid catalyst is fixed in the reactor by a certain support means, the solid catalyst and regular corrugated sheets are effectively combined together to form a plurality of catalyst fillers having a hollow structure, and a material discharged from the bottom of the EMC reactive distillation column 2 enters the DMC recovery column 3;
  a part of a material extracted from the top of the DMC recovery column 3 is sent back to the pre-reactor 1 to continue to react with ethanol, and the other part of the material extracted from the top of the DMC recovery column 3 enters the anti-disproportionation reactor 4 to react with dimethyl carbonate to generate ethyl methyl carbonate; mixed esters (dimethyl carbonate, ethyl methyl carbonate and diethyl carbonate) produced by the anti-disproportionation reactor 4 are conveyed to the DMC recovery column 3 to recover unreacted dimethyl carbonate;
  a material discharged from the bottom of the DMC recovery column 3 enters the crude separation column 5, a gas phase at the top of the crude separation column 5 provides a partial heat source for a reboiler 19 of the DMC recovery column;
  a material discharged from the top of the crude separation column 5 enters the EMC light component removal column 6, a material discharged from the top of the EMC light component removal column 6 enters the DMC recovery column 3, a material discharged from the bottom of the EMC light component removal column 6 enters the EMC heavy component removal column 7, a material extracted from the side of the EMC heavy component removal column 7 is electronic-grade EMC (by means of side extraction, light and heavy components can be removed in one column, trace light components are accumulated at the top of the column, heavy components are extracted from the bottom of the column and qualified products are obtained by side extraction), a material discharged from the bottom of the EMC heavy component removal column 7 enters the crude separation column 5, and a material discharged from the top of the EMC heavy component removal column 7 enters the EMC light component removal column 6;

a material extracted from the bottom of the crude separation column 5 enters the DEC light component removal column 8, a material extracted from the top of the DEC light component removal column 8 enters the crude separation column 5; a material extracted from the bottom of the DEC light component removal column 8 enters the DEC heavy component removal column 9, a material extracted from the top of the DEC heavy component removal column 9 is sent back to the DEC light component removal column 8, a material extracted from the bottom of the DEC heavy component removal column 9 is a DEC high-boiling residue, a part of a material extracted from the side of the DEC heavy component removal column 9 is an electronic-grade DEC product, and a part of the material extracted from the side of the DEC heavy component removal column 9 is conveyed to the anti-disproportionation reactor 4, and a gas phase at the top of the DEC light component removal column 8 provides a partial heat source for a reboiler 28 of the DEC heavy component removal column; and a material discharged from the top of the EMC reactive distillation column 2, namely the azeotrope of DMC and methanol enters the pressurizing column 10, a gas phase at the top of the pressurizing column 10 provides a partial heat source for a reboiler 23 of the EMC reactive distillation column, a material discharged from the top of the pressurizing column 10 enters the atmospheric column 11, a material discharged from the bottom of the pressurizing column 10 enters the DMC refining column 13, a material discharged from the bottom of the DMC refining column 13 is a DMC high-boiling residue, a material discharged from the top of the DMC refining column 13 enters the pressurizing column 10, a material extracted from the side of the DMC refining column 13 is industrial-grade DMC, a side extraction outlet of the DMC refining column 13 communicates with the pre-reactor 1, a material discharged from the top of the atmospheric column 11 enters the pressurizing column 10, a gas phase at the top of the atmospheric column 11 is converted into secondary steam under the action of a compressor 25 of the atmospheric column to provide a heat source for a reboiler 36 of the atmospheric column, a material discharged from the bottom of the atmospheric column 11 enters the methanol refining column 12, a gas phase at the top of the methanol refining column 12 is converted into secondary steam under the action of a compressor 30 of a methanol column to provide a heat source for a reboiler 29 of the methanol refining column, a material extracted from the side of the methanol refining column 12 is a methanol by-product, a material extracted from the top of the methanol refining column 12 enters the pressurizing column 10, and a material extracted from the bottom of the methanol refining column 12 is reboiled, and the material extracted from the bottom of the column enters a reboiling tank, and is discharged to the outside.

The mechanical vapor recompression for energy saving in the refining process of ethyl methyl carbonate includes an EMC compressor 26, secondary steam compressed by the EMC compressor 26 is delivered to a reboiler 34 of the EMC light component removal column, and a reboiler 35 of the EMC heavy component removal column, respectively, and is heated, and then the heated material passes through the following two branches, respectively;

a branch 1, where the steam is cooled into water after passing through the reboiler 34 of the EMC light component removal column, and enters a condenser 38 of the EMC light component removal column for heat exchange and partial vaporization, and the generated steam continues to enter the EMC compressor 26;

a branch 2, where the steam is cooled into water after passing through the reboiler 35 of the EMC heavy component removal column, and enters a condenser 37 of the EMC heavy component removal column for heat exchange and partial vaporization, and the generated steam continues to enter the EMC compressor 26; and recycling is performed through the branch 1 and the branch 2.

Example 3

Figure 3:
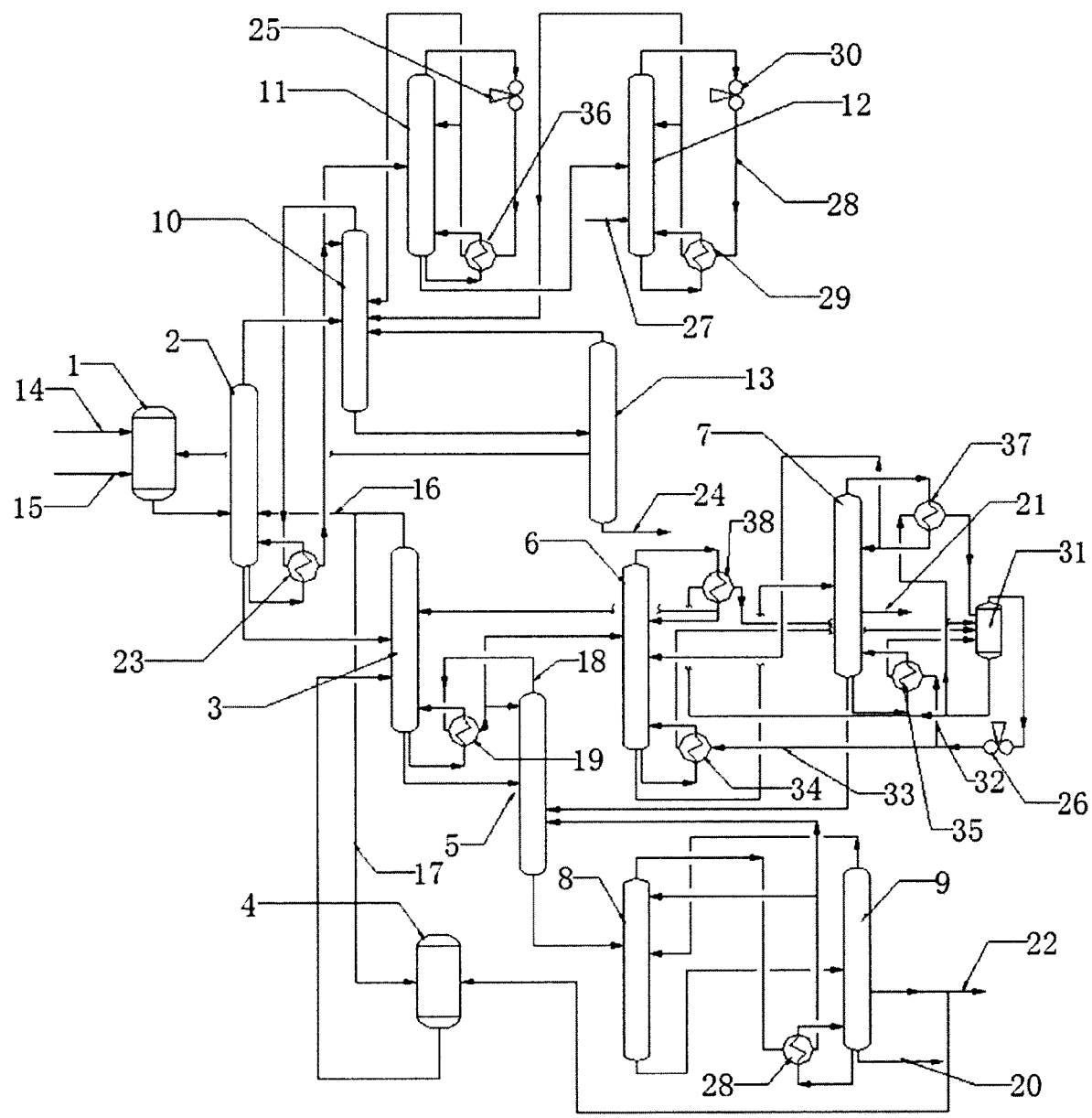
FIG. 3 is a diagram of a system in Example 3 of the present disclosure.

An energy-saving system for preparing electronic-grade carbonate, as shown in FIG. 3, includes a pre-reactor 1, an EMC reactive distillation column 2, a DMC recovery column 3, an anti-disproportionation reactor 4, a crude separation column 5, an EMC light component removal column 6, an EMC heavy component removal column 7, a DEC light component removal column 8, a DEC heavy component removal column 9, a pressurizing column 10, an atmospheric column 11, a methanol refining column 12 and a DMC refining column 13; wherein the pre-reactor 1 is connected to an industrial-grade dimethyl carbonate feeding pipeline 14 and an ethanol feeding pipeline 15, a discharge port at the bottom of the pre-reactor 1 communicates with a feed port at the lower middle part of the EMC reactive distillation column 2 through a pipeline, and the EMC reactive distillation column 2 is provided with a catalytic filler containing a solid catalyst;

a discharge port at the bottom of the EMC reactive distillation column 2 is connected via a pipeline to a feed inlet at the middle of the DMC recovery column 3; a top extraction outlet of the DMC recovery column 3 communicates with a feed inlet of a raw material DMC of the pre-reactor 1 via a first connection pipeline 16, and the top extraction outlet of the DMC recovery column 3 communicates with a feed inlet of a raw material DMC of the anti-disproportionation reactor 4 via a second connection pipeline 17; and a discharge port of mixed esters (dimethyl carbonate, ethyl methyl carbonate and diethyl carbonate) at the bottom of the anti-disproportionation reactor 4 communicates with a feed inlet at the lower part of the DMC recovery column 3 via a pipeline;

a discharge port at the bottom of the DMC recovery column 3 communicates with a feed inlet at the middle of the crude separation column 5 via a pipeline, a column top gas phase pipeline 18 of the crude separation column 5 is subjected to heat exchange with the reboiler 19 of the DMC recovery column, and a liquid phase port at the lower part of the reboiler 19 of the DMC recovery column is connected to an inlet of a reflux tank of the crude separation column 5;

a discharge port at the top of the crude separation column 5 communicates with a feed inlet at the middle of the EMC light component removal column 6, a discharge port at the top of the EMC light component removal column 6 is connected to the feed inlet at the middle of the DMC recovery column 3, a discharge port at the bottom of the EMC light component removal column 6 is connected to a feed inlet at the middle of the EMC heavy component removal column 7, a distillation section of the EMC heavy component removal column 7 is provided with an electronic-grade EMC side extraction outlet 21 for extraction of electronic-grade EMC, and a discharge port at the bottom of the EMC heavy component removal column 7 communicates with the feed inlet at the middle of the crude separation column 5;

a discharge port at the bottom of the crude separation column 5 communicates with a feed inlet at the upper part of the DEC light component removal column 8 via a pipeline, a bottom extraction outlet of the DEC light component removal column 8 communicates with a feed inlet at the middle of the DEC heavy component removal column 9, a top extraction outlet of the DEC heavy component removal column 9 communicates with a feed inlet at the upper part of the DEC light component removal column 8, a bottom extraction outlet of the DEC heavy component removal column 9 is connected with a DEC high-boiling residue discharge pipeline 20, a side extraction outlet of the DEC heavy component removal column 9 is connected to an electronic-grade DEC product output pipeline 22, the electronic-grade DEC product output pipeline 22 is also connected to a pipeline of a raw material DEC of the anti-disproportionation reactor 4 through a pipeline, a gas phase pipeline at the top of the DEC light component removal column 8 is subjected to heat exchange with the reboiler 28 of the DEC heavy component removal column, and a liquid phase port at lower part of the reboiler 28 of the DEC heavy component removal column is connected to an inlet of a reflux tank 40 of the DEC light component removal column 8;

a discharge port at the top of the EMC reactive distillation column 2 is connected to a feed inlet at the middle of the pressurizing column 10 through a pipeline, a gas phase at the top of the pressurizing column 10 is connected to the reboiler 23 of the EMC reactive distillation column through a heat exchange pipeline, the reboiler 23 of the EMC reactive distillation column communicates with a feed inlet of the pressurizing column 10 and a feed inlet of the atmospheric column 11 through pipelines, respectively, a discharge port at the bottom of the pressurizing column 10 communicates with a feed inlet at the middle of the DMC refining column 13, a discharge port at the bottom of the DMC refining column 13 is connected to a DMC high-boiling residue discharge pipeline 24, a side extraction outlet of the DMC refining column 13 communicates with the pre-reactor 1, a gas phase outlet at the top of the atmospheric column 11 is connected to an inlet of the compressor 25 of the atmospheric column through a pipeline, an outlet of the compressor 25 of the atmospheric column is connected to the reboiler 36 of the atmospheric column, a part of the reboiler 36 of the atmospheric column is connected by a pipeline to a reflux port at the top of the atmospheric column 11 and a part is connected to a feed inlet at the middle-upper part of the pressurizing column 10; and a discharge part at the bottom of the atmospheric column 11 is connected to a feed inlet at the middle of the methanol refining column 12, a gas phase outlet at the top of the methanol refining column 12 communicates with an inlet of the compressor 30 of the methanol column via a pipeline, an outlet of the compressor 30 of the methanol column communicates with the reboiler 29 of the methanol refining column via a pipeline, the reboiler 29 of the methanol refining column communicates with the middle of the methanol refining column 12 and the middle of the atmospheric column 11 via pipelines, respectively, and a side extraction outlet of the methanol refining column 12 is connected to a methanol by-product discharge pipeline 27.

The mechanical vapor recompression for energy saving in the refining process of ethyl methyl carbonate includes an EMC compressor 26 and a gas-liquid separation tank 31, a gas phase outlet of the gas-liquid separation tank 31 is connected to the EMC compressor 26, an outlet of the EMC compressor 26 is connected via a first branch pipe 32 to a heat exchange interlayer of the reboiler 35 of the EMC heavy component removal column, an outlet of the heat exchange interlayer of the reboiler 35 of the EMC heavy component removal column is connected to a water inlet of the gas-liquid separation tank 31, the outlet of the EMC compressor 26 is connected via a second branch pipe 33 to a heat exchange interlayer of the reboiler 34 of the EMC light component removal column, and an outlet of the heat exchange interlayer of the reboiler 34 of the EMC light component removal column, and the outlet of the heat exchange interlayer of the reboiler 35 of the EMC heavy component removal column are connected to the water inlet of the gas-liquid separation tank 31; and a water outletsof the gas-liquid separation tank 31 is connected to a water inlet of a heat exchange interlayer of the condenser 37 of the EMC heavy component removal column, and a water inlet of a heat exchange interlayer of the condenser 38 of the EMC light component removal column via pipelines, respectively, and a steam outlet of the heat exchange interlayer of the condenser 37 of the EMC heavy component removal column, and a steam outlet of the heat exchange interlayer of the condenser 38 of the EMC light component removal column are connected to a steam inlet of the gas-liquid separation tank 31 via pipelines, respectively.

Example 4

This example provides a further description of operating parameters of each device based on Example 2.

Operating parameters of the pre-reactor 1 are as follows:

| Name | Parameter range | Optimal operating parameter |
|---|---|---|
| Operating temperature (° C.) | 110-130 | 115 |
| Operating pressure kPaA | 300-900 | 400~500 |

Operating parameters of the anti-disproportionation reactor 4 are as follows:

| Name | Parameter range | Optimal operating parameter |
|---|---|---|
| Operating temperature (° C.) | 110-130 | 115 |
| Operating pressure kPaA | 300-900 | 400~500 |

Operating parameters of the EMC reactive distillation column 2 are as follows:

| Name | Parameter range | Optimal operating parameter |
|---|---|---|
| Column top temperature (° C.) | 64 | / |
| Column bottom temperature (° C.) | 105 | / |
| Operating pressure kPaA | atmospheric pressure | / |
| Reflux ratio | 2~6 | 4 |
| The number of theoretical plates | 30~60 | 50 |
| Feed position | 30~50 | 40 |
| Side extraction | / | / |

Operating parameters of the DMC recovery column 3 are as follows:

| Name | Parameter range | Optimal operating parameter |
|---|---|---|
| Column top temperature (° C.) | 50~55 | 52 |
| Column bottom temperature (° C.) | 75~80 | 77 |
| Operating pressure kPaA | 25~40 | 30 |
| Reflux ratio | 5~10 | 7 |
| The number of theoretical plates | 30~60 | 50 |
| Feed position | 10~30 | 20 |
| Side extraction | / | / |

Operating parameters of the crude separation column 5 are as follows:

| Name | Parameter range | Optimal operating parameter |
|---|---|---|
| Column top temperature (° C.) | 101~150 | 106 |
| Column bottom temperature (° C.) | 128~135 | 130 |
| Operating pressure kPaA | 90~200 | 30 |
| Reflux ratio | 1~10 | 3 |
| The number of theoretical plates | 30~60 | 50 |
| Feed position | 10~30 | 20 |
| Side extraction | / | / |

Operating parameters of the EMC light component removal column 6 are as follows:

| Name | Parameter range | Optimal operating parameter |
|---|---|---|
| Column top temperature (° C.) | 50~60 | 55 |
| Column bottom temperature (° C.) | 70~80 | 75 |
| Operating pressure kPaA | 20~30 | 25 |
| Reflux feed ratio | 1~5 | 3 |
| The number of theoretical plates | 50~60 | 50 |
| Feed position | 10~30 | 20 |
| Side extraction | / | / |

Operating parameters of the EMC heavy component removal column 7 are as follows:

| Name | Parameter range | Optimal operating parameter |
|---|---|---|
| Column top temperature (° C.) | 50~60 | 55 |
| Column bottom temperature (° C.) | 70~80 | 75 |
| Operating pressure kPaA | 20~30 | 25 |
| Reflux feed ratio | 1~5 | 3 |
| The number of theoretical plates | 50~60 | 50 |
| Feed position | 40~50 | 45 |
| Side extraction | 20 | / |

Operating parameters of the DEC light component removal column 8 are as follows:

| Name | Parameter range | Optimal operating parameter |
|---|---|---|
| Column top temperature (° C.) | 50~60 | 55 |
| Column bottom temperature (° C.) | 128~150 | 130 |
| Operating pressure kPaA | 101~200 | 105 |
| Reflux feed ratio | 1~5 | 3 |
| The number of theoretical plates | 50~60 | 50 |
| Feed position | 10~30 | 20 |
| Side extraction | / | / |

Operating parameters of the DEC heavy component removal column 9 are as follows:

| Name | Parameter range | Optimal operating parameter |
|---|---|---|
| Column top temperature (° C.) | 85~90 | 88 |
| Column bottom temperature (° C.) | 90~100 | 95 |
| Operating pressure kPaA | 20~40 | 30 |
| Reflux feed ratio | 1~5 | 3 |
| The number of theoretical plates | 50~60 | 50 |
| Feed position | 40~50 | 45 |
| Side extraction | 20 | / |

Operating parameters of the pressurizing column 10 are as follows:

| Name | Parameter range | Optimal operating parameter |
|---|---|---|
| Column top temperature (° C.) | 130~150 | 140 |
| Column bottom temperature (° C.) | 170~190 | 95 |
| Operating pressure kPaA | 700~1000 | 900 |
| Reflux feed ratio | 1~5 | 3 |
| The number of theoretical plates | 50~60 | 50 |
| Feed position | 30~50 | 40 |
| Side extraction | / | / |

Operating parameters of the atmospheric column 11 are as follows:

| Name | Parameter range | Optimal operating parameter |
|---|---|---|
| Column top temperature (° C.) | 64 | / |
| Column bottom temperature (° C.) | 66 | / |
| Operating pressure kPaA | 101~110 | 105 |
| Reflux feed ratio | 1~5 | 3 |
| The number of theoretical plates | 50~60 | 50 |
| Feed position | 30~50 | 40 |
| Side extraction | / | / |

Operating parameters of the DMC refining column 13 are as follows:

| Name | Parameter range | Optimal operating parameter |
|---|---|---|
| Column top temperature (° C.) | 91 | / |
| Column bottom temperature (° C.) | 94 | / |
| Operating pressure kPaA | 101~110 | 105 |
| Reflux feed ratio | 1~5 | 3 |
| The number of theoretical plates | 50~60 | 50 |
| Feed position | 30~50 | 40 |
| Side extraction | 20 | / |

Operating parameters of the methanol refining column 12 are as follows:

| Name | Parameter range | Optimal operating parameter |
|---|---|---|
| Column top temperature (° C.) | 64 | / |
| Column bottom temperature (° C.) | 66 | / |
| Operating pressure kPaA | 101~110 | 105 |
| Reflux feed ratio | 1~5 | 3 |
| The number of theoretical plates | 50~60 | 50 |
| Feed position | 30~50 | 40 |
| Side extraction | 20 | / |

The energy consumption of this example is shown in the following table:

| Name | Energy consumption per ton of product (ton of steam/ton of product) | Power consumption (kW-h/ton of product) |
|---|---|---|
| Example 4 | 3.237 | 210 |
| Non-energy-saving process | 8.72 | 74 |

Wherein a compression ratio of the EMC compressor is 2.4, and a compression ratio of the compressor of the atmospheric column is 1.45, and a compression ratio of the compressor of the methanol column is 1.45.

Comparative Example

Comparative Example 1.1

Patent: CN112142599A Low-Energy-Consumption and Green Carbonate Product Production Process and System

| Name | Energy consumption per ton of product (ton of steam/ton of product) | Power consumption (kW-h/ton of product) |
|---|---|---|
| This patent | 4.97 | with a heat pump, and no consumption |
| Non-energy-saving process | 10 | / |

Comparative Example 1.2

Patent: CN106699565A Device for energy saving of dimethyl carbonate device

This device mainly consists of a reaction column, a pressurizing column and an atmospheric column, and produces dimethyl carbonate (non-electronic grade).

| Name | Energy consumption per ton of product (ton of steam/ton of product) | Power consumption (kW-h/ton of product) |
|---|---|---|
| This patent | 2.25 | 209.5 |
| Non-energy-saving process | 3.5 | / |

Comparative Example 1.3

Patent: CN110845334A Device and Method for Preparing Battery-Grade Ethyl Methyl Carbonate from Dimethyl Carbonate and Ethanol This device mainly consists of three columns: a reaction column, a diethyl carbonate removal column and an ethyl methyl carbonate refining column. Dimethyl carbonate and methanol are not separated, and there is no refining of diethyl carbonate.

| Name | Energy consumption per ton of product (ton of steam/ton of product) | Power consumption (kW-h/ton of product) |
| --- | --- | --- |
| CN110845334A | 5.2 | 100 |
| Example 1 | 3 | 160 |
| Example 2 | 2.9 | 168 |

The above descriptions are only preferred embodiments of the present disclosure, and it should be noted that for a person of ordinary skill in the art, a number of improvements and modifications can also be made without departing from the principles of the present disclosure, and these improvements and modifications shall also be considered as the scope of protection of the present disclosure.

What is claimed is:

1. An energy-saving method for preparing electronic-grade carbonate, comprising a reaction process, a recovery process of dimethyl carbonate, a crude separation process, a refining process of ethyl methyl carbonate, a refining process of diethyl carbonate, and a refining process of dimethyl carbonate and methanol; wherein industrial-grade dimethyl carbonate and anhydrous ethanol enter the reaction process after being preheated by a preheater, and are subjected to an esterification reaction under the action of a catalyst to obtain a mixture containing dimethyl carbonate, ethyl methyl carbonate and diethyl carbonate, and an azeotrope of dimethyl carbonate and methanol; the mixture containing dimethyl carbonate, ethyl methyl carbonate and diethyl carbonate enters the recovery process of dimethyl carbonate to recover unreacted dimethyl carbonate; a mixture of ethyl methyl carbonate and diethyl carbonate then enters the crude separation process to obtain crude ethyl methyl carbonate and crude diethyl carbonate; the crude ethyl methyl carbonate is subjected to the refining process of ethyl methyl carbonate to obtain electronic-grade ethyl methyl carbonate, and the crude diethyl carbonate is subjected to the refining process of diethyl carbonate to obtain electronic-grade diethyl carbonate; the azeotrope of dimethyl carbonate and methanol is subjected to the refining process of dimethyl carbonate and methanol to obtain dimethyl carbonate and methanol;

in the reaction process, industrial-grade dimethyl carbonate and ethanol enter an EMC reactive distillation column after being preheated by a pre-reactor, the EMC reactive distillation column is provided with a solid catalyst to catalyze the reaction, and a material discharged from the bottom of the EMC reactive distillation column enters a DMC recovery column;

in the recovery process of dimethyl carbonate, a part of a material extracted from the top of the DMC recovery column is sent back to the EMC reactive distillation column, and the other part of the material extracted from the top of the DMC recovery column enters an anti-disproportionation reactor; DMC/EMC/DEC produced by the anti-disproportionation reactor is conveyed to the DMC recovery column; a material discharged from the bottom of the DMC recovery column enters a crude separation column;

in the crude separation process, material discharged from the top of the crude separation column enters an EMC light component removal column, and a material extracted from the bottom of the crude separation column enters a DEC light component removal column;

in the refining process of ethyl methyl carbonate, a material discharged from the top of the EMC light component removal column enters the DMC recovery column, a material discharged from the bottom of the EMC light component removal column enters an EMC heavy component removal column, a material extracted from the side of the EMC heavy component removal column is electronic-grade EMC, a material discharged from the bottom of the EMC heavy component removal column enters the crude separation column, and a material discharged from the top of the EMC heavy component removal column enters the EMC light component removal column;

in the refining process of diethyl carbonate, a material extracted from the bottom of the DEC light component removal column enters a DEC heavy component removal column, a material extracted from the top of the DEC heavy component removal column is sent back to the DEC light component removal column, a material extracted from the bottom of the DEC heavy component removal column is a DEC high-boiling residue, a part of a material extracted from the side of the DEC heavy component removal column is an electronic-grade DEC product, and a part of the material extracted from the side of the DEC heavy component removal column is conveyed to the anti-disproportionation reactor; and in the refining process of dimethyl carbonate and methanol, a material discharged from the top of the EMC reactive distillation column, namely the azeotrope of DMC and methanol enters a pressurizing column, a material discharged from the top of the pressurizing column enters an atmospheric column, a material discharged from the bottom of the pressurizing column enters a DMC refining column, a material discharged from the DMC refining column is a DMC high-boiling residue, a material discharged from the top of the atmospheric column enters the pressurizing column, a material discharged from the bottom of the atmospheric column enters a methanol refining column, and a material extracted from the side of the methanol refining column is a methanol by-product.

2. The energy-saving method for preparing electronic-grade carbonate of claim 1, wherein the reaction process is thermally integrated and coupled with the refining process of dimethyl carbonate and methanol for energy saving, the recovery process of dimethyl carbonate is thermally integrated and coupled with the crude separation process for energy saving, the refining process of ethyl methyl carbonate uses thermal integration and coupling for energy saving, the refining process of dimethyl carbonate and methanol uses mechanical vapor recompression for energy saving, and the refining process of ethyl methyl carbonate uses mechanical vapor recompression for energy saving.

3. The energy-saving method for preparing electronic-grade carbonate of claim 2, wherein a gas phase at the top of the crude separation column provides a partial heat source for a reboiler of the DMC recovery column.

4. The energy-saving method for preparing electronic-grade carbonate of claim 2, wherein a gas phase at the top of the pressurizing column provides a partial heat source for a reboiler of the EMC reactive distillation column.

5. The energy-saving method for preparing electronic-grade carbonate of claim 2, wherein a gas phase at the top of the atmospheric column is converted into secondary steam under the action of a compressor of the atmospheric column to provide a heat source for a reboiler of the atmospheric column.

6. The energy-saving method for preparing electronic-grade carbonate of claim 2, wherein a gas phase at the top of the methanol refining column is converted into secondary steam under the action of a compressor of a methanol column to provide a heat source for a reboiler of the methanol refining column.

7. The energy-saving method for preparing electronic-grade carbonate of claim 2, wherein the mechanical vapor recompression for energy saving in the refining process of ethyl methyl carbonate comprises an EMC compressor, secondary steam compressed by the EMC compressor is delivered to a reboiler of the EMC light component removal column and a reboiler of the EMC heavy component removal column, respectively, and is heated, and then the heated material passes through the following two branches, respectively;
  a branch 1 where the steam is cooled into water after passing through the reboiler of the EMC light component removal column, and enters a condenser of the EMC light component removal column for heat exchange and partial vaporization, and the generated steam continues to enter the EMC compressor;
  a branch 2 where the steam is cooled into water after passing through the reboiler of the EMC heavy component removal column, and enters a condenser of the EMC heavy component removal column for heat exchange and partial vaporization, and the generated steam continues to enter the EMC compressor; and
  recycling is performed through the branch 1 and the branch 2.

8. The energy-saving method for preparing electronic-grade carbonate of claim 1, wherein
  operating parameters of the pre-reactor are as follows: an operating temperature is 110-130° C., and an operating pressure is 300-900 kPaA;
  operating parameters of the anti-disproportionation reactor are as follows: an operating temperature is 110-130° C., and an operating pressure is 300-900 kPaA;
  operating parameters of the EMC reactive distillation column are as follows: a column top temperature is 64° C., a column bottom temperature is 105° C., and an operating pressure is an atmospheric pressure;
  operating parameters of the DMC recovery column are as follows: a column top temperature is 50~55° C., a column bottom temperature is 75~80° C., an operating pressure is 25~40 kPaA, a reflux ratio is 5~10, the number of theoretical plates is 30~60, and feed positions are at 10~30th theoretical plates;
  operating parameters of the crude separation column are as follows: a column top temperature is 101~150° C., a column bottom temperature is 128~135° C., an operating pressure is 90~200 kPaA, a reflux ratio is 1~10, the number of theoretical plates is 30~60, and feed positions are at 10~30th theoretical plates;
  operating parameters of the EMC light component removal column are as follows: a column top temperature is 50~60° C., a column bottom temperature is 70~80° C., an operating pressure is 20~30 kPaA, a reflux feed ratio is 1~5, the number of theoretical plates is 50~60, and feed positions are at 10~30th theoretical plates;
  operating parameters of the EMC heavy component removal column are as follows: a column top temperature is 50~60° C., a column bottom temperature is 70~80° C., an operating pressure is 20~30 kPaA, a reflux feed ratio is 1~5, the number of theoretical plates is 50~60, and feed positions are at 40~50th theoretical plates;
  operating parameters of the DEC light component removal column are as follows: a column top temperature is 50~60° C., a column bottom temperature is 128~150° C., an operating pressure is 101~200 kPaA, the number of theoretical plates is 50~60, and feed positions are at 10~30th theoretical plates;
  operating parameters of the DEC heavy component removal column are as follows: a column top temperature is 85-90° C., a column bottom temperature is 90~100° C., a reflux feed ratio is 1~5, the number of theoretical plates is 50~60, feed positions are at 40~50th theoretical plates, and side extraction is performed at a 20th theoretical plate;
  operating parameters of the pressurizing column are as follows: a column top temperature is 170-190° C., a column bottom temperature is 700-1000° C., a reflux feed ratio is 1~5, the number of theoretical plates is 50~60, and feed positions are at 30~50th theoretical plates;
  operating parameters of the atmospheric column are as follows: a column top temperature is 64° C., a column bottom temperature is 66° C., an operating pressure is 101~110 kPaA, a reflux feed ratio is 1~5, the number of theoretical plates is 50~60, and feed positions are at 30~50th theoretical plates;
  operating parameters of the DMC refining column are as follows: a column top temperature is 91° C., a column bottom temperature is 94° C., an operating pressure is 101~110 kPaA, a reflux feed ratio is 1~5, the number of theoretical plates is 50~60, feed positions are at 30~50th theoretical plates, and side extraction is performed at a 20th theoretical plate; and
  operating parameters of the methanol refining column are as follows: a column top temperature is 64° C., a column bottom temperature is 66° C., an operating pressure is 101~110 kPaA, a reflux feed ratio is 1~5, the number of theoretical plates is 50~60, feed positions are at 30~50th theoretical plates, and side extraction is performed at a 20th theoretical plate.

* * * * *